United States Patent
Slack et al.

(10) Patent No.: US 6,393,091 B1
(45) Date of Patent: May 21, 2002

(54) METHODS AND APPARATUS FOR NON-UNIFORM TEMPORAL CARDIAC IMAGING

(75) Inventors: Christopher C. Slack; Jianying Li, both of New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/460,261

(22) Filed: Dec. 13, 1999

(51) Int. Cl.⁷ .......................... A61B 6/00; G01N 23/00; G21K 1/22; H05G 1/60
(52) U.S. Cl. ............................................. 378/8; 378/95
(58) Field of Search ....................... 378/8, 95

(56) References Cited

U.S. PATENT DOCUMENTS

| | | |
|---|---|---|
| 3,952,201 A | 4/1976 | Hounsfield |
| 4,182,311 A | 1/1980 | Seppi et al. |
| 4,530,109 A | 7/1985 | Klausz |
| 4,641,328 A | 2/1987 | Fujise |
| 4,994,965 A | 2/1991 | Crawford et al. |
| 5,533,085 A | 7/1996 | Sheehan et al. |
| 5,544,212 A | 8/1996 | Heuscher |
| 5,602,891 A | 2/1997 | Pearlman |
| 5,751,782 A | 5/1998 | Yoshitome |
| 5,832,051 A * | 11/1998 | Lutz ............................... 378/8 |
| 6,154,516 A | 11/2000 | Heuscher et al. |
| 6,275,560 B1 * | 8/2001 | Blake et al. ................... 378/8 |

FOREIGN PATENT DOCUMENTS

| | | |
|---|---|---|
| EP | 0 370 341 A2 | 5/1990 |
| EP | 1 013 225 A1 | 6/2000 |
| EP | 1 050 272 A1 | 11/2000 |
| EP | 1 072 224 A2 | 1/2001 |
| EP | 1 088 517 A1 | 4/2001 |
| EP | 1 090 586 A2 | 4/2001 |
| WO | WO 00/30539 | 6/2000 |

OTHER PUBLICATIONS

Woodhouse et al., "Coronary Arteries: Retrospective Cardiac Gating Technique to Reduce Cardiac Motion Artifact at Spiral CT," Radiology, Aug. 1997, pp. 566–569.

Spraggins et al., "Retrospective Cardiac Gating Requiring No Physiological Monitoring," undated, one page.

Broderick et al., "Measurement of Coronary Artery Calcium with Dual–Slice Helical CT Compared with Coronary Angiography: Evaluation of CT Scoring Methods, Interobserver Variations, and Reproducibility," AJR:167, Aug. 1996, pp. 439–444.

* cited by examiner

Primary Examiner—Robert H. Kim
Assistant Examiner—Courtney Thomas
(74) Attorney, Agent, or Firm—Carl B. Horton, Esq.; Armstrong Teasdale LLP

(57) ABSTRACT

A method for imaging a heart of a patient utilizing a CT imaging system includes steps of assigning a scanning priority to phases of a representative cardiac cycle of the patient's heart, selecting phases of the cardiac cycle for scanning in accordance with the assigned scanning priority, and obtaining image slices of the patient's heart corresponding the selected phases of the cardiac cycle. The method can be performed by a CT imaging system including an EKG machine to record EKG data.

24 Claims, 2 Drawing Sheets

METHODS AND APPARATUS FOR NON-UNIFORM TEMPORAL CARDIAC IMAGING

BACKGROUND OF THE INVENTION

This invention relates generally to methods and apparatus for computed tomography cardiac imaging, and more particularly to methods and apparatus for non-uniform temporal recording of cardiac images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Computed tomography images of the heart are useful for a number of diagnostic and surgical purposes. At least one known procedure requires that a collection of cardiac phase images be obtained. However, the process of obtaining such a collection is complicated by the fact that the heart does not beat in a uniform temporal fashion. During a single cardiac cycle, there are some times during which the volume of the heart is changing faster than average, and some times during which the volume changes more slowly than average. Currently, when temporal cardiac scanning is performed on a CT scanner, images corresponding to several phases of a cardiac cycle are captured at evenly spaced intervals. The images that are acquired are evenly spaced in time, resulting in an oversampling of certain phases of the cardiac cycle. Other phases are undersampled. Thus, temporal resolution is impaired. It would therefore be desirable for CT imaging apparatus and methods to optimize a collection of cardiac phase images by avoiding over- and undersampling.

BRIEF SUMMARY OF THE INVENTION

There is therefore provided, in one embodiment, a method for imaging a heart of a patient utilizing a CT imaging system including steps of assigning a scanning priority to phases of a representative cardiac cycle of the patient's heart, selecting phases of the cardiac cycle for scanning in accordance with the assigned scanning priority, and obtaining image slices of the patient's heart corresponding the selected phases of the cardiac cycle.

The above described embodiment results in a non-uniform temporal scan that provides improved temporal resolution. Moreover, both undersampling and oversampling of phases is avoided by the assignment of priorities, resulting in a more optimized collection of cardiac images.

DETAILED DESCRIPTION OF THE INVENTION

Figure 1:
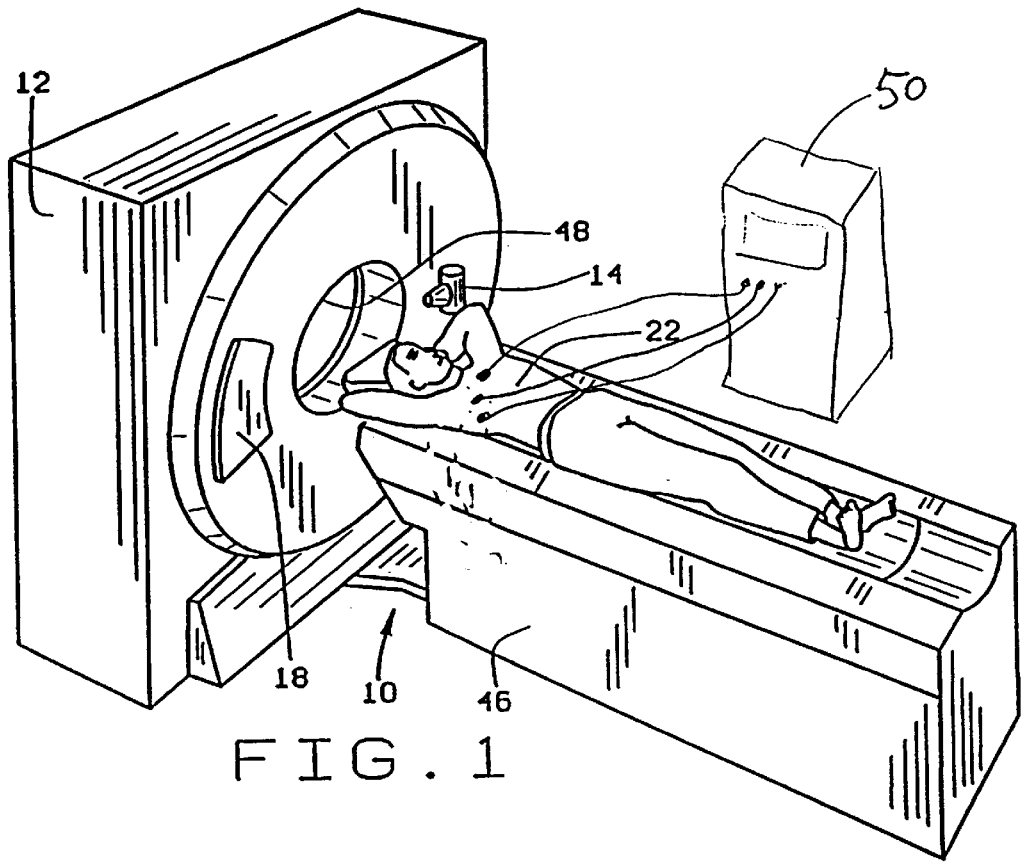
FIG. 1 is a pictorial view of a CT imaging system.
Figure 2:
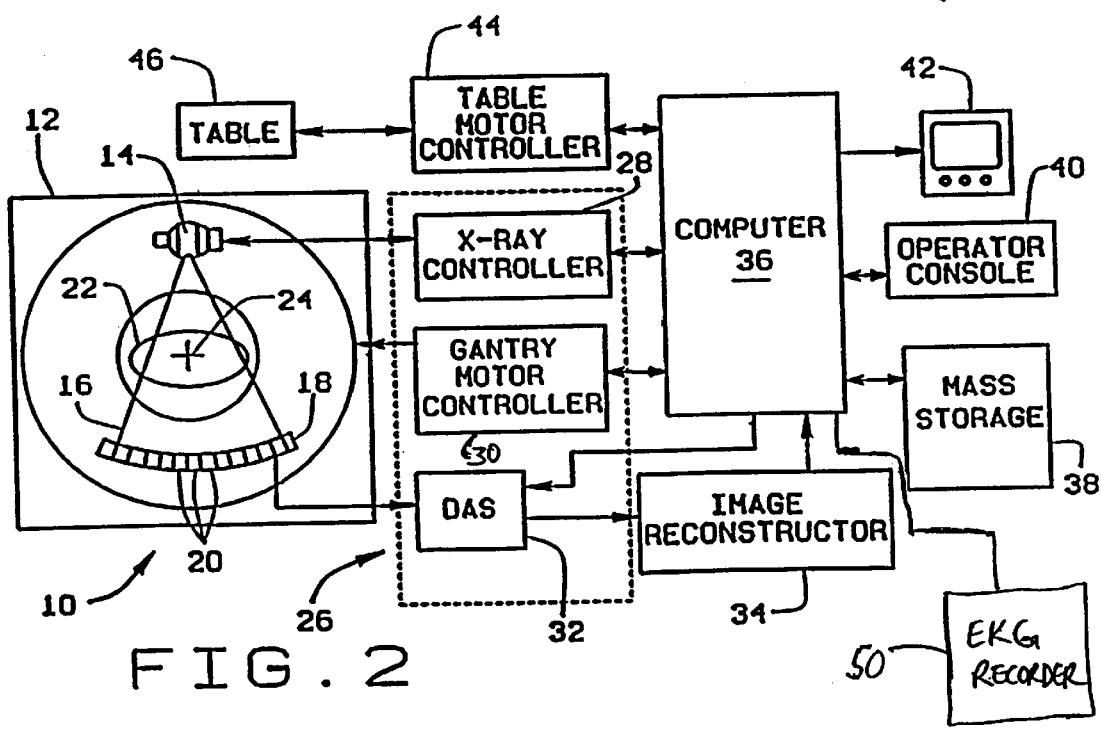
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48 in a z-axis direction.

Figure 3:
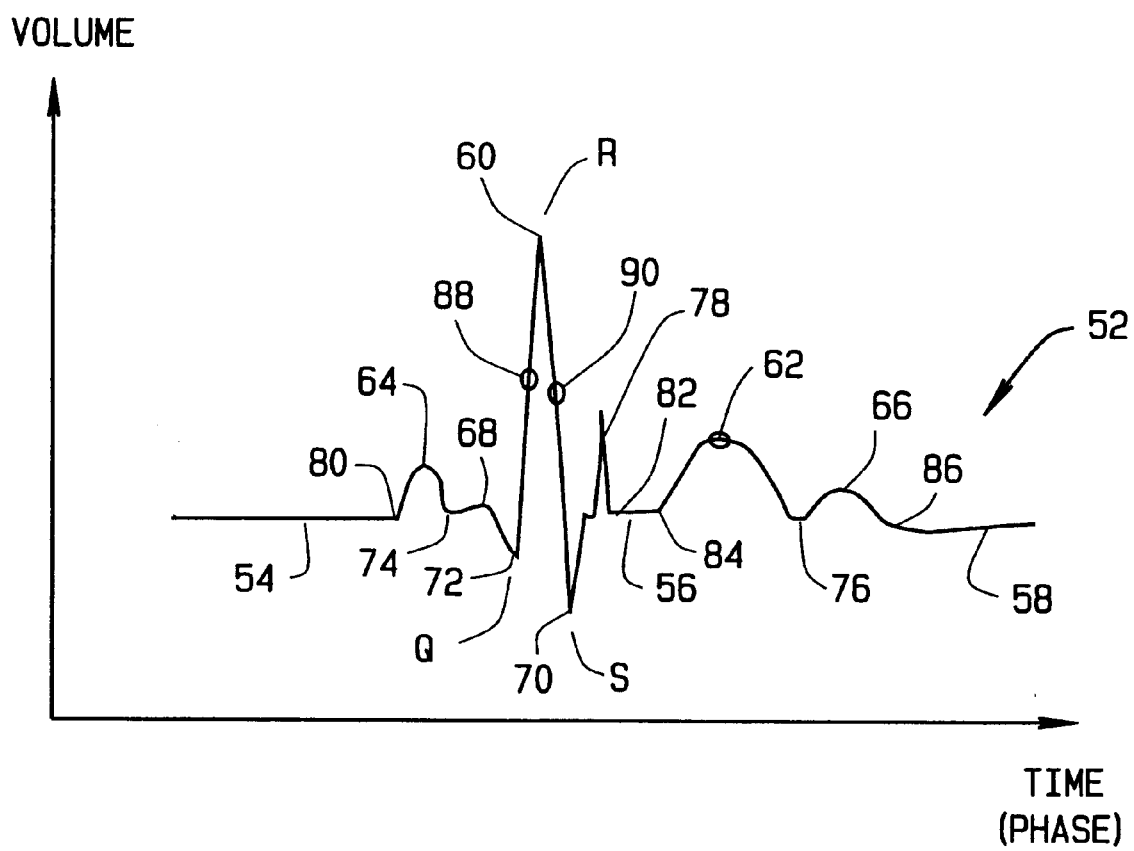
FIG. 3 is a graphical representation of a cardiac cycle as a function of time.

In one embodiment of the present invention, a non-uniform sampling technique is used to optimize temporal resolution of a collection of cardiac phase images. Sampling points are determined utilizing a signal representative of volumetric change of the heart, such as an EKG signal from EKG machine 50. Before scanning patient 22, data representing a typical cardiac cycle 52 of the heart of patient 22 is obtained utilizing EKG machine 50. For example, a representative cardiac cycle 52 is computed from EKG signal data obtained from a plurality of normal cardiac cycles. The plurality of cycles are averaged to obtain the representative normal cycle, such as that illustrated in FIG. 3.

The representative cycle is analyzed for changes that occur at each phase in cardiac cycle 52. In particular, flat or baseline sections 54, 56, 58 are identified, as are local maxima 60, 62, 64, 66, 68 and minima 70, 72, 74, 76. Times at which local maxima 60, 62, 64, 66, 68 and minima 70, 72, 74, 76 occur relative to a reference time in cardiac cycle 52 are obtained by utilizing second derivative information from cardiac waveform 52. Voltages representing volume changes of the heart of patient 22 are produced by EKG machine 50. EKG cycle 52 thus determined represents volume changes of the heart. Rankings are assigned based upon a distance at each local maxima and minima from a baseline section 54, 55, 58 of waveform 52.

In one embodiment, data of representative cardiac cycle waveform 52 is filtered to reduce temporal and spatial noise. For example, cardiac cycle 52 is analyzed to determine volume changes and rates of change. Based on these determinations, a threshold is applied to cardiac waveform 52 to eliminate changes in the waveform that are small enough to be ignored. The threshold is selected by computing an estimated noise level or by estimating a noise level by visual inspection of waveform 52. Small volume changes in waveform 52 below the threshold are replaced with a flat baseline. For example, points 68, 74, and 76 are ignored. Short temporal impulses 78, such as those having shorter duration than a temporal resolution of CT imaging device 10, also are ignored. For example, impulses of duration less than about 100 ms are ignored. In another embodiment, thresholds are selected in accordance with a maximum desired temporal and spatial resolution. In one embodiment, thresholding is performed prior to locating maxima and minima of cardiac waveform 52.

After filtering waveform 52, all remaining local maxima 60, 62, 64, 66 and local minima 70, 72, 74 in a resulting waveform 52 are found. Each points 60, 62, 64, 66, 70, 72, 74 corresponds to different phases of representative cardiac cycle 52 of patient 22. Priority values are assigned to the phases of each of the local maxima 60, 62, 64, 66 and minima 70, 72, 74 in accordance with volume differences from baseline 54, 56, 58, the volume distances being represented by vertical distances in cardiac waveform 52. In one embodiment, greater volume differences are assigned greater priority. One such ordering of priority, in order from highest to lowest, is 60, 70, 62, 72, 64, and 66.

In one embodiment, at least one transition point 78, 80, 82, 84 or 86 on baseline 54, 56, 58 is also selected for scanning and imaging. Transition points 78, 80, 82, 84, and 86 occur at phases in which a volume change just begins to occur after a period of little or no motion. However, it is only necessary to scan at a single transition point, e.g., point 78, because the heart volume of patient 22 is approximately the same at each transition point 78, 80, 82, 84, and 86. A single imaging scan at the selected transition point is used to represent the heart at each of transition points 78, 80, 82, 84, 86. In one embodiment, a transition point is given a high priority above that of all maxima and minima.

In one embodiment, additional phases are assigned scanning priorities in accordance with temporal and spatial gradients. For example, phases 88 and 90 are selected between minima and maxima 72 and 60, and 60 and 70, respectively. Phases 88 and 90 or other such additional phases are selected when doing so is determined to be advantageous for reconstruction of images. Priority values are then assigned to the selected additional phases 88, 90. When there are fewer minima and maxima than phases, all minima and maxima phases are selected. Also, additional phases such as 88 and 90 are selected in order of priority (for example, those at which a magnitude of the slope of waveform 52 is greatest) until a total of the selected phases is equal to the number of sectors. On the other hand, when there are more minima and maxima than sectors, only the highest priority minima and maxima points are selected, up to a maximum number of available sectors. For example, only those minima and maxima having the greatest volume change as indicated by a vertical distance from baseline 54, 56, 58 are selected for scanning. More generally, phases are sorted in accordance with their assigned priority, and a number of points N of highest priority are selected, where N is a number of phases desired for generating images.

A cine cardiac scan (i.e., a scan during which gantry 12 rotates, but table 46 is held stationary) is then performed by CT imaging system 10 at a time interval corresponding to each of the N points along waveform 52. A reference phase from an EKG machine 50 sensing cardiac cycles of patient 22 is used, in one embodiment, to establish a reference for scanning times. For example, scanning times are referenced to occurrences of R peaks sensed by CT imaging system 10 in an EKG signal received from EKG machine 50.

An axial image slice is generated for each phase of a cine scan when CT imaging system 10 is a single-slice imaging system. When a collection of phases for more than one image plane or slice is desired, the cine scanning step is repeated for each plane or slice after table 46 is stepped to a new location. Collection of phases for more than one image plane or slice is further facilitated, in one embodiment, by utilizing a multi-slice imaging system as CT imaging system 10. Suitable adjustments are made in the stepping distance of table 46 in accordance with slice thicknesses and a number of slices collected simultaneously during a scan.

In one embodiment, N phases are not sufficient to include a desired temporal midpoint or phase, such as 88, during acquisition. In this embodiment, linear interpolations between phases preceding and following midpoint 88 are performed to fill in a temporal coverage gap in coverage. The newly interpolated slice is considered an additional phase for purposes of the invention.

Data is then displayed as image frames. As used herein, for a 2-D temporal display, a "frame" consists of a single scanned image. For a 3-D temporal display, a "frame" is a collection comprising a plurality of such images representing different image slices or planes. In the case of a 3-D temporal display, each image in the collection corresponds to the same phase in the patient's cardiac cycle. In one embodiment, a number of identical frames F to display for each phase $P_n$ is written as:

$$F=(\text{Pos}(P_{n+1})-\text{Pos}(P_n))\times FR,$$

where:
F=a number of phases displayed for phase n;
$P_n$=phase n;
Pos($P_n$)=a temporal position of phase n; and
FR=display frame rate.

With frames displayed in this manner, an animated display representing the heart of patient 22 is produced from an optimized collection of cardiac phase images. The resulting animated images have improved temporal resolution.

In one embodiment, CT imaging system 10 is programmed to perform steps described above. For example, computer 36 receives an EKG signal from EKG machine 50 for analysis. Software or firmware operating computer 36 averages an EKG waveform over a plurality of cycles and assigns scanning priorities in accordance with measurable characteristics of the average waveform. For example, software operating computer 36 assigns priorities strictly in accordance with computed second derivative values of a cardiac waveform to recognize maxima and minima, and also locates maximum and minimum slopes of the cardiac waveform. In addition, a baseline phase is also selected for scanning. Scanning is performed automatically by gating scan cycles with observed R-peaks of a cardiac cycle from an EKG taken during scanning. Image reconstructor 34 and/or computer 36 then compute images for display on CRT 42.

From the preceding description of various embodiments of the present invention, it is evident that CT cardiac images having improved temporal resolution are obtained by avoiding oversampling and undersampling of cardiac phases. Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for imaging a heart of a patient utilizing a CT imaging system, said method comprising the steps of:
   assigning a scanning priority to phases of a representative cardiac cycle of the patient's heart in accordance with cardiac volume distances from a baseline volume;
   selecting phases of the cardiac cycle for scanning in accordance with the assigned scanning priority; and
   obtaining image slices of the patient's heart corresponding the selected phases of the cardiac cycle.

2. A method in accordance with claim 1 further comprising obtaining EKG data of the patient's heart, and wherein assigning a scanning priority in accordance with cardiac volume distances from a baseline volume comprises the step of assigning a priority to local maxima and minima of the heart volume in accordance with heart volumes indicated by the EKG data.

3. A method in accordance with claim 2 wherein obtaining EKG data of the patient's heart comprises the steps of recording a plurality of complete cardiac cycles of the patient's heart and computing the representative cardiac cycle of the patient's heart utilizing the plurality of complete cardiac cycles.

4. A method in accordance with claim 3 wherein computing the representative cardiac cycle comprises the step of averaging the plurality of complete cardiac cycles.

5. A method in accordance with claim 2 wherein obtaining image slices of the patient's heart comprises performing a cine scan of the patient's heart.

6. A method in accordance with claim 2 wherein assigning a scanning priority to phases of a representative cardiac cycle of the patient's heart comprises the step of assigning a scanning priority in accordance with cardiac volume distances from a baseline volume and also in accordance with temporal and spatial gradients of the cardiac data.

7. A method in accordance with claim 6 further comprising the step of interpolating between at least a pair of selected phases to select an additional phase for scanning.

8. A method in accordance with claim 2 and further comprising the step of filtering the EKG data in accordance with criteria selected to reduce temporal and spatial noise.

9. A method in accordance with claim 2 wherein at least one of the selected phases is a phase corresponding to a baseline volume of the patient's heart.

10. A method in accordance with claim 1 and further comprising the step of displaying data as animated image frames, wherein a number of identical frames F to display for each phase $P_n$ is written as:

$$F=(\text{Pos}(P_{n+1})-\text{Pos}(P_n))\times FR,$$

where:
   F=a number of phases displayed for phase n;
   $P_n$=a phase n;
   Pos($P_n$)=a temporal position of phase n; and
   FR=a display frame rate.

11. A method in accordance with claim 10 wherein displaying data as animated image frames comprises the step of displaying frames consisting of one image slice.

12. A method in accordance with claim 10 wherein displaying data as animated image frames comprises the step of displaying frames comprising a plurality of image slices representing different planes at a single phase of the patient's cardiac cycle.

13. A CT imaging system for imaging a heart of a patient, said imaging system including a radiation source and detector configured to rotate in an imaging plane around the patient, the detector being configured to sense the projected x-rays that pass the heart of the patient, said imaging system configured to:
   assign a scanning priority to phases of a representative cardiac cycle of the patient's heart in accordance with cardiac volume distances from a baseline volume;
   select phases of the cardiac cycle for scanning in accordance with the assigned scanning priority; and
   obtain image slices of the patient's heart corresponding the selected phases of the cardiac cycle.

14. A system in accordance with claim 13 further configured to obtain EKG data of the patient's heart, and wherein said system being configured to assign a scanning priority in accordance with cardiac volume distances from a baseline volume comprises said system being configured to assign a priority to local maxima and minima of the heart volume in accordance with heart volumes indicated by the EKG data.

15. A system in accordance with claim 14 wherein said system being configured to obtain EKG data of the patient's heart comprises said system being configured to record a plurality of complete cardiac cycles of the patient's heart and to compute the representative cardiac cycle of the patient's heart utilizing the plurality of complete cardiac cycles.

16. A system in accordance with claim 15 wherein said system being configured to compute the representative cardiac cycle comprises said system being configured to average the plurality of complete cardiac cycles.

17. A system in accordance with claim 14 wherein said system being configured to obtain image slices of the patient's heart comprises said system being configured to perform a cine scan of the patient's heart.

18. A system in accordance with claim 14 wherein said system being configured to assign a scanning priority to phases of a representative cardiac cycle of the patient's heart comprises said system being configured to assign a scanning priority in accordance with cardiac volume distances from a baseline volume and also in accordance with temporal and spatial gradients of the cardiac data.

19. A system in accordance with claim 18 further configured to interpolate between at least a pair of selected phases to select an additional phase for scanning.

20. A system in accordance with claim 14 configured to filter the EKG data in accordance with criteria selected to reduce temporal and spatial noise.

21. A system in accordance with claim 14 wherein at least one of the selected phases is a phase corresponding to a baseline volume of the patient's heart.

22. A system in accordance with claim 13 further configured to display data as animated image frames, wherein a number of identical frames F to display for each phase $P_n$ is written as:

$$F=(Pos(P_{n+1})-Pos(P_n)) \times FR,$$

where:

F=a number of phases displayed for phase n;

$P_n$=a phase n;

$Pos(P_n)$=a temporal position of phase n; and

FR=a display frame rate.

23. A system in accordance with claim 22 wherein said system being configured to display data as animated image frames comprises said system being configured to display frames consisting of one image slice.

24. A system in accordance with claim 22 wherein said system being configured to display data as animated image frames comprises said system being configured to display frames comprising a plurality of image slices representing different planes at a single phase of the patient's cardiac cycle.

* * * * *